United States Patent [19]

Häfelé et al.

[11] Patent Number: 4,988,970

[45] Date of Patent: Jan. 29, 1991

[54] SEMICONDUCTOR FOR A RESISTIVE GAS SENSOR HAVING A HIGH RESPONSE SPEED

[75] Inventors: Edelbert Häfelé, Karlsruhe; Karl-Heinz Härdtl, Hagenbach; Andreas Müller, Heidelberg; Ulrich Schönauer, Karlsruhe, all of Fed. Rep. of Germany

[73] Assignee: Kernforschungszentrum Karlsruhe GmbH, Karlsruhe, Fed. Rep. of Germany

[21] Appl. No.: 423,445

[22] PCT Filed: Jul. 7, 1989

[86] PCT No.: PCT/DE88/00418

§ 371 Date: Sep. 28, 1989

§ 102(e) Date: Sep. 28, 1989

[87] PCT Pub. No.: WO89/00686

PCT Pub. Date: Jan. 26, 1989

[30] Foreign Application Priority Data

Jul. 11, 1987 [DE] Fed. Rep. of Germany ....... 3723051

[51] Int. Cl.$^5$ ............................................. H01C 7/00
[52] U.S. Cl. ................................................... 338/34
[58] Field of Search ................ 338/34, 35; 324/65 R; 73/23, 27 R

[56] References Cited

U.S. PATENT DOCUMENTS

| | | | |
|---|---|---|---|
| 3,951,603 | 4/1976 | Obayashi et al. | 23/232 E |
| 3,952,567 | 4/1976 | Shinagawa et al. | 338/34 X |
| 4,507,643 | 3/1985 | Sunano et al. | 338/34 |
| 4,677,414 | 6/1987 | Yates | 338/34 |

FOREIGN PATENT DOCUMENTS 0055104 6/1982 European Pat. Off. .
2149121 6/1985 United Kingdom .

Primary Examiner—Bruce A. Reynolds
Assistant Examiner—Marvin Lateef
Attorney, Agent, or Firm—Spencer & Frank

[57] ABSTRACT

Semiconductors for resistive gas sensors or resistive semiconductor gas sensors with high speed of reaction are disclosed. These semiconductors are appropriate to measure the partial pressure of oxygen and reducing gases in any predetermined measurement range between $10^{-30}$ and about 1 bar or in the whole of this measurement range, their resistance changes being caused by a volume effect. In particular, these semiconductors have a layer less than 100 μm thick, predetermined geometric structure and clearly marked marginal zones. A specially doped semiconductor composed of perowskit having the general formula $A'_xA_{1-x}Z_1B'_yB_{1-y}Z_2O_3$ is applied on a substrate with a paste of an organic base material by a thick film technique. By adding or removing at least one element or by using two different semiconductors the characteristic curve is clearly traced.

8 Claims, 6 Drawing Sheets

SEMICONDUCTOR FOR A RESISTIVE GAS SENSOR HAVING A HIGH RESPONSE SPEED

The invention relates to semiconductors for a resistive gas sensor or, more precisely, a resistive semiconductor gas sensor having a high response speed as defined in the preambles of claims 1, 2 and 3, respectively.

To measure the partial pressure of oxygen and reducing gases (such as, for example, NO, CO, $C_3H_8$, etc.), specific mixed oxides, the so-called perovskites, are particularly suitable semiconductors.

Perovskite semiconductors for gas sensors and their production by sintering was disclosed by Obayashi et al in U.S. Pat. No. 3,951,603 and in U.S. Pat. No. 3,953,173, by Sakurai et al in U.S. Pat. No. 4,044,601 and by Perry et al in U.S. Pat. No. 4,221,827.

In contrast to semiconductors made of tin oxide or similar materials in which the surface resistance changes as a function of the partial pressure of the gas being measured, the change in resistance in perovskite semiconductors is based on a volume effect; i.e. the semiconductor resistance changes as a function of the concentration of the gas being measured in that oxygen is diffused in the semiconductor.

The addition of reducing gases to the gas being measured causes the oxygen concentration in the semiconductor to be reduced due to the diffusion of oxygen to the surface of the solid body; the addition of oxygen to the gas being measured causes a corresponding increase in the oxygen concentration in the semiconductor due to the diffusion of oxygen into the solid body.

Since, however, after a change in the partial pressure of the gas being measured, oxygen must be able to diffuse into or out of the semiconductor material such semiconductors, in the interest of a high response speed, should be as thin as possible as the diffusion time for the oxygen is proportional to the square of the layer thickness. Such semiconductors are substantially insensitive to surface soiling and can also be used in rougher environments.

Sintering permits the production of semiconductors with minimum layer thicknesses between 20 and 50 $\mu m$, usually, however, 500 $\mu m$. The sintering method is frequently employed as a simple manufacturing process for gas sensor semiconductors which are produced in small numbers.

For mass production, the high energy costs caused by the long duration of the sintering process and the additional costs for the required subsequent treatment of sawing, grinding and polishing become a weighty factor.

For higher requirements with respect to response speed, the semiconductors could be produced in a thin-film process. In the past, dielectric materials have been applied to capacitor plates in this way. In this case, the substances constituting the semiconductor would be applied to a substrate by sputtering. This would permit the realization of very small layer thicknesses.

However—as a result of the high vacuum procedure this process is very complicated and thus expensive so that it is hardly suitable for the mass production of semiconductor sensors.

Due to the short free path lengths of the particles to be sputtered on and the collision processes resulting therefrom, no accurate geometric structures with sharply defined edge zones can be produced even if templates are employed.

Another serious drawback is that the number of substances to be sputtered on is limited; it is not possible to produce repeatedly doped perovskites in this manner.

As tests have shown, the perovskite semiconductors described in the literature so far do not exhibit an unequivocal characteristic (change in resistance as a function of the concentration of the gas being measured) over a greater range of measuring gas partial pressures of several orders of magnitude. Usually, the characteristic passes through a minimum so that two different measuring gas concentration ranges exist in which the semiconductor has the same electrical resistance.

Such semiconductors can be employed only in a measuring gas concentration range in which the characteristic is not ambiguous.

It is the object of the invention to produce resistive semiconductors for gas sensors which have a high response speed, are suitable for measuring the partial pressure of oxygen and reducing gases and whose change in resistance is based on a volume effect.

In particular, the layer thickness of these semiconductors is to be less than the layer thickness of prior art resistive semiconductors produced by sintering and should lie below 100 $\mu m$, preferably between about 1 and 20 $\mu m$.

The manufacturing process should be flexible in such a manner that it is possible to produce with the same processing aids semiconductors having greatly differing compositions. Moreover, the semiconductors are to have predetermined geometric structures and sharply defined edge zones.

Employing semiconductors produced in this way, gas sensors are to be provided which are suitable for measuring the partial pressure of oxygen and reducing gases in any desired, given measuring range between $10^{-30}$ and about 1 bar and over this entire measuring range.

This is accomplished according to the invention by the characterizing features of claims 1 to 3.

The thick-film process is particularly suitable for the realization of semiconductor layer thicknesses below 100 $\mu m$, particularly between about 1 and 20 $\mu m$, thus considerably increasing the response speed of such gas sensors.

A particularly suitable thick-film process is the screen-printing process which, in the past, has been used primarily as a high-quality color printing process for paper, cloth and similar materials.

Moreover, immersion coating and spraying on under pressure a paste composed of a powdered mixed oxide and an organic paste base can be employed advantageously in the thick-film process, with defined geometric structures having sharply delimited edge zones being produced with the aid of a template.

The thick-film process constitutes a simple and effective manufacturing method which is particularly suitable for the mass production of semiconductor sensors since the costs for operating this process are noticeably less compared to the sintering and thin-film processes, and subsequent treatment is either not required at all or only to a minor extent.

A particular advantage is that semiconductor materials of the most varied compositions having any desired number of components can be processed in mass production with the same processing aids. This is not possible in particular, with the thin-film process.

By doping perovskites and positively deviating from the stoichiometry and by using at least two different semiconductors, gas sensors can be produced which can be employed in a certain given measuring range or in a measuring range covering many powers of ten.

The invention will now be described in greater detail by way of the following examples.

EXAMPLE 1

The paste is manufactured of 70% $SrTiO_3$ (HST-2/HPST-2 made by Fuji) and 30% paste base material (including ethyl cellulose, butyl Carbitol acetate and α-terpineol). Applying the layer by means of screen-printing, then traversing a temperature profile up to 1330° C. as shown in FIG. 1.

EXAMPLE 2

FIG. 2 shows the shift of the minimum of the characteristic and thus of the measuring range of a semiconductor sensor due to directed deviations from its stoichiometry.

The figure shows the characteristics of perovskite semiconductors having an Sr/Ti ratio of 1.0000 (curve 1), 0.9990 (curve 2) and 0.9950 (curve 3) at 1000° C.

EXAMPLE 3

FIG. 3 shows the shift of the minimum of the characteristic and thus of the measuring range of a semiconductor sensor by directed doping with chromium and aluminum, respectively. The test temperature is 1000° C. Curve 1 shows the characteristic for $CaCr_{0.0025}Ti_{0.9975}O_3$, which coincides with the characteristic of $CaAl_{0.0025}Ti_{0.9975}O_3$. Curve 2 shows the characteristic of $CaCr_{0.0055}Ti_{0.9945}O_3$ which coincides with the characteristic of $CaAl_{0.0055}Ti_{0.0045}O_3$.

EXAMPLE 4

A given perovskite semiconductor is assumed to have a characteristic for oxygen corresponding to characteristic 1 in FIG. 4 that is ambiguous over the measuring range. Another semiconductor 2 is assumed to have a characteristic 2 which has a minimum at a lower oxygen concentration than characteristic 1. Such a semiconductor can be produced, for example, by doping semiconductor 1 with acceptors, i.e. by replacing part of element A by a mono-valent element from Group A'.

If $p(O_2A)$ is to be detected, the value $\sigma_{BA}$ furnished by characteristic 1 may originate from point A as well as from point B. If now a second semiconductor having, for example, a higher acceptor doping, is connected in series, it can be determined by means of its characteristic 2 which of the two points A or B furnishes the conductivity value $\sigma_{BA}$. If semiconductor 2 emits a greater voltage $U_2$ than semiconductor 1 ($U_2$ $U_1$), $p(O_2A)$ is detected; if 2 furnishes a lower voltage ($U_2$ $U_1$), $p(O_2B)$ is detected. The associated basic circuit diagram is shown in FIG. 5.

EXAMPLE 5

Another example for measuring a gas component with the aid of several semiconductors is the arrangement sketched in FIG. 6.

To measure reducing gases (in this case, carbon monoxide), one of two identical semiconductor sensors is coated with a layer which is catalytically active for the total oxidation. A thin, porous platinum layer is suitable as the catalytically active layer.

The arrangement is composed of two sensor resistors S1 and S2 and two identical prior art resistors R and R'. The difference in sensor resistances can be calculated according to the following formula by way of a given reference voltage $U_{ref}$ and the voltages $U_1$ and $U_2$ to be measured:

$$R = S1 - S2 = R\left(\frac{U_1}{U_{ref} - U_1} - \frac{U_2}{U_{ref} - U_2}\right)$$

Figure 1:
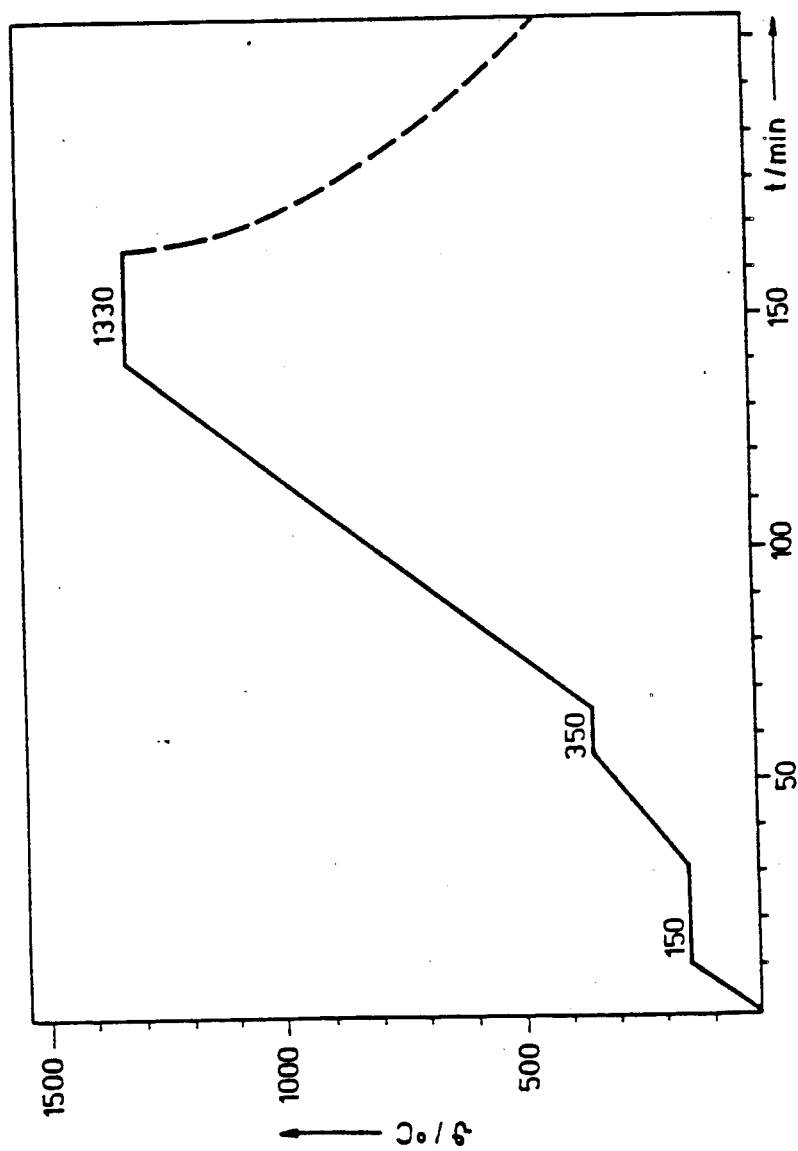
Figure 2:
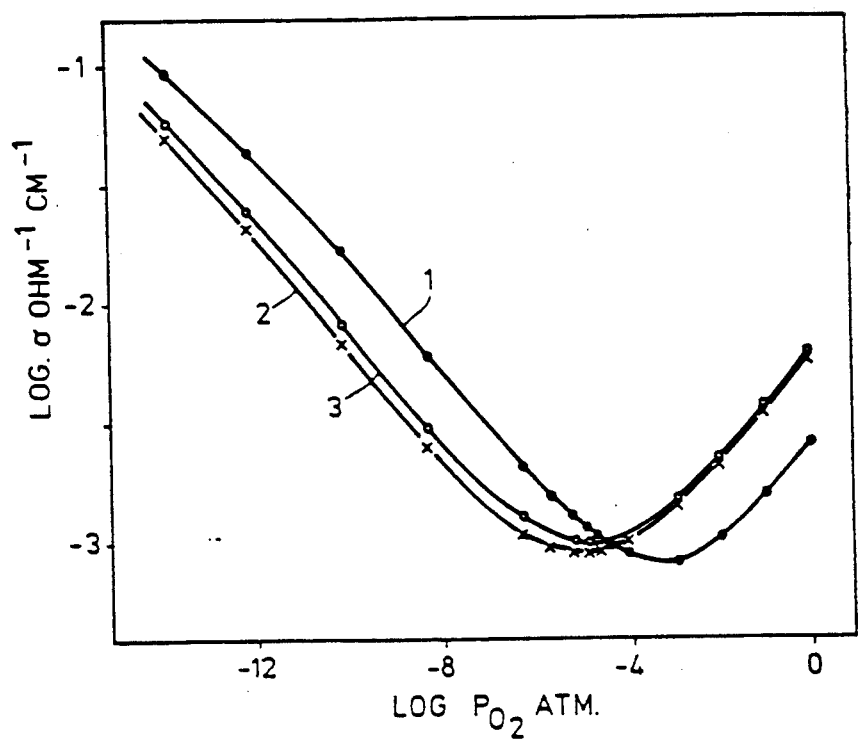
Figure 3:
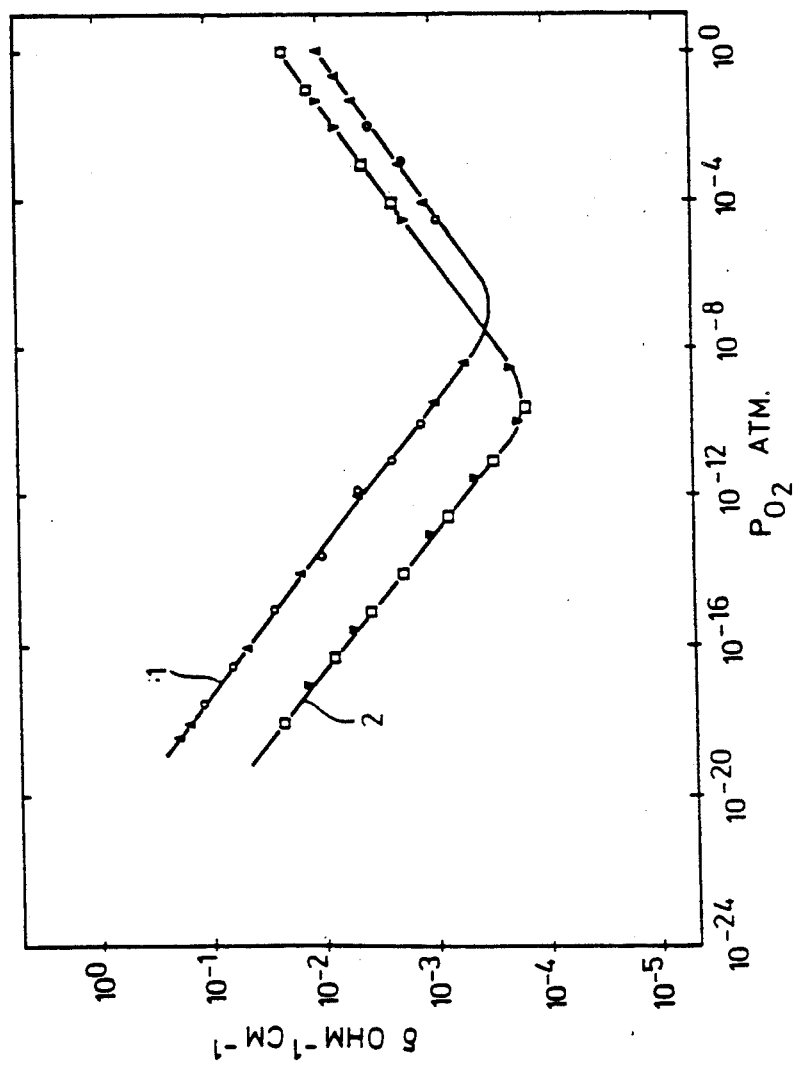
Figure 4:
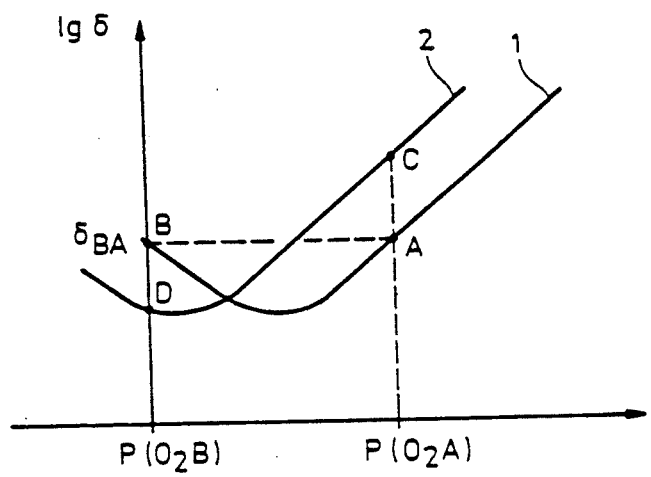
Figure 5:
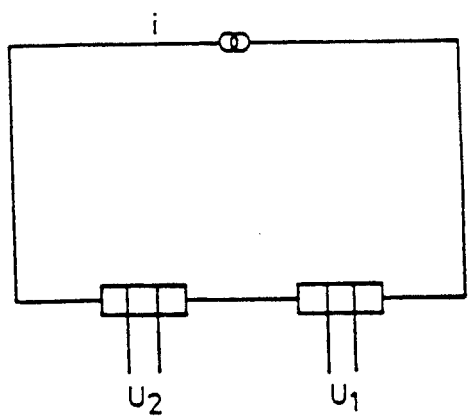
Figure 6:
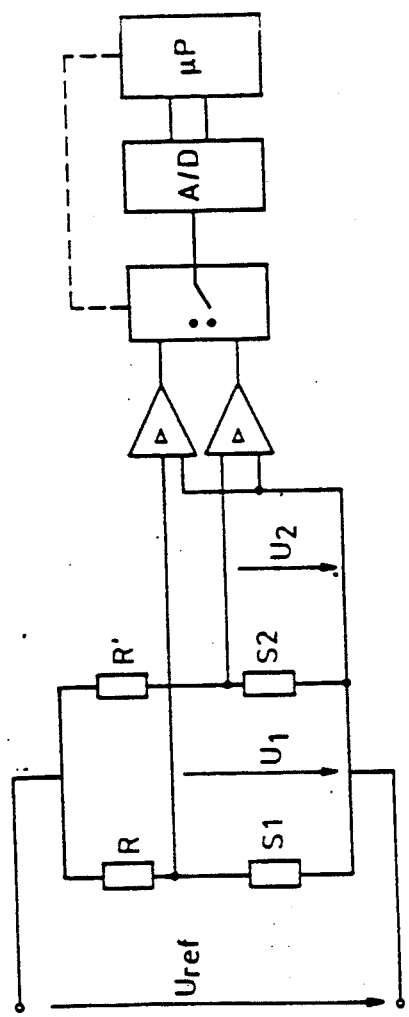
Figure 7:
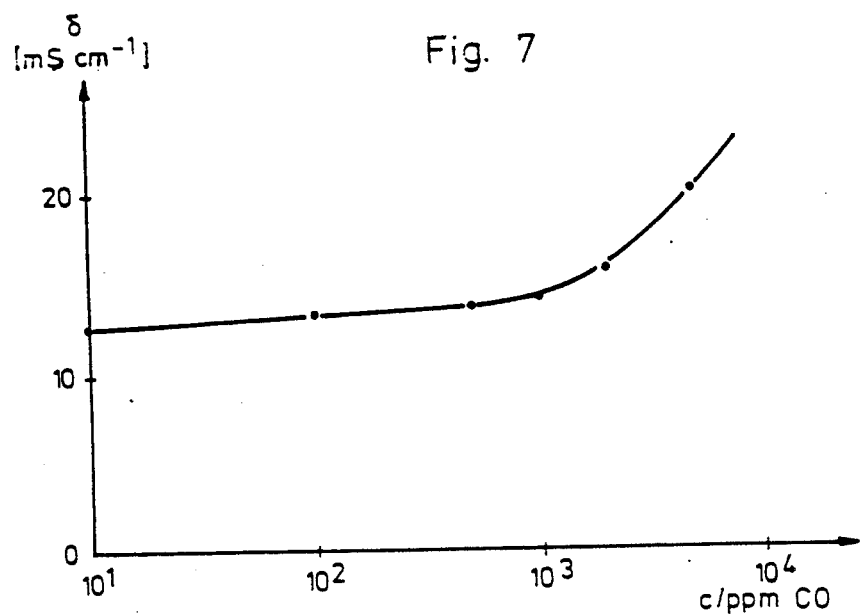
FIG. 7 shows the dependence of the sensor conductivity on the carbon monoxide concentration at a temperature of 1000° C. and with an oxygen content of 5% in nitrogen for an $SrTiO_3$ semiconductor.
Figure 8:
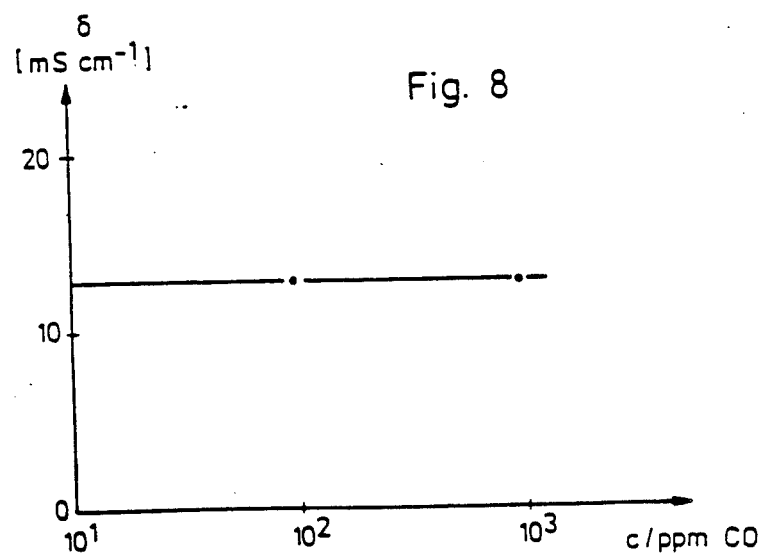
FIG. 8 shows that under otherwise identical conditions, a sensor provided with a catalytic cover layer has a conductivity which is independent of the carbon monoxide content.

An arrangement corresponding to FIG. 6 is particularly able to selectively determine the concentration of the reducing gas component even with fluctuating oxygen content in the gas phase.

We claim:

1. Semiconductor for a resistive gas sensor having a high response speed for a determination of the partial pressure of oxygen and reducing gases, the semiconductor comprising a doped perovskite of the general composition $A'_xA_{1-x-z1}B'_yB_{1-y-z2}O_3$, where A', A, B' and B are metal ions and the parameters z1 and z2 represent stoichiometry indices, characterized in that the value of x lies in a range from >0 to 0.05, the value of y in a range from >0 to 0.1 and the absolute values of z1 and z2 lie in a range between 0 and 0.002.

2. Method of producing the semiconductor of claim 1, characterized in that
   (a) the perovskite is pulverized and is processed into a paste together with an organic paste base material;
   (b) the paste is applied onto a substrate with the aid of the thick-film process, with a layer thickness of less than 100 μm, preferably between 1 and 20 μm, being maintained.

3. Method according to claim 2, characterized in that the screen-printing process is employed as the thick-film process.

4. Method according to claim 2, characterized in that immersion coating is employed as the thick-film process with the substrate being masked by means of a template.

5. Method according to claim 2, characterized in that a method is employed as the thick-film process in which the pasty semiconductor material is sprayed under pressure onto the substrate which has been masked by a template.

6. Method according to one of claim 2, characterized in that the semiconductor applied in the thick-film process is subjected to a temperature treatment in such a manner that, in a first heating phase, the liquid components of the organic paste base material are evaporated, in a second heating phase at higher temperatures, the solid components of the organic paste base material are combusted without residue and this is followed by a third heating phase whose duration in time and maximum temperature are selected in such a manner that the semiconductor material is prevented from separating from the substrate.

7. Method of determining the partial pressure of oxygen and reducing gases by means of a semiconductor as defined in claim 1, characterized in that the characteristic of the semiconductor is made unequivocal in the measuring range by changing the doping of at least one element of group A' and/or B' or by changing the stoichiometry indices z1 and/or z2.

8. Method of producing a gas sensor for a determination of the partial pressure of oxygen and reducing gases in the measuring range between $10^{-30}$ and 1 bar while employing a semiconductor according to claim 1 whose characteristic in this range includes an extreme value, characterized in that (a) at least two different semiconductors are employed and the electrical resistances of these semiconductors are utilized for a determination of the partial pressure of the gas being measured;

(b) the semiconductors are successively applied to a substrate by repeated use of a thick-film process, with the layer thicknesses being less than 100 μm, preferably between 1 and 20 μm.

* * * * *

UNITED STATES PATENT AND TRADEMARK OFFICE
CERTIFICATE OF CORRECTION

PATENT NO. : 4,988,970

DATED : January 29th, 1991

INVENTOR(S) : Edelbert HÄFELE et al.

It is certified that error appears in the above-identified patent and that said Letters Patent is hereby corrected as shown below:

ON TITLE PAGE:

The last name of the first-named inventor should read -- Häfele --.

Under [22], the PCT filing date should read -- July 7th, 1988 --.

Signed and Sealed this

Second Day of June, 1992

*Attest:*

DOUGLAS B. COMER

*Attesting Officer*     Acting Commissioner of Patents and Trademarks